United States Patent
Chen

(10) Patent No.: US 9,564,145 B2
(45) Date of Patent: Feb. 7, 2017

(54) SPEECH INTELLIGIBILITY DETECTION

(71) Applicant: DSP Group LTD., Herzeliya (IL)

(72) Inventor: Yaakov Chen, Rishon Le-tzion (IL)

(73) Assignee: DSP Group Ltd., Herzliya (IL)

( * ) Notice: Subject to any disclaimer, the term of this patent is extended or adjusted under 35 U.S.C. 154(b) by 66 days.

(21) Appl. No.: 14/318,705

(22) Filed: Jun. 30, 2014

(65) Prior Publication Data
US 2015/0010156 A1 Jan. 8, 2015

Related U.S. Application Data

(60) Provisional application No. 61/843,396, filed on Jul. 7, 2013.

(51) Int. Cl.
| | |
|---|---|
| G10L 21/02 | (2013.01) |
| A61B 5/00 | (2006.01) |
| A61B 5/22 | (2006.01) |
| G10L 25/69 | (2013.01) |
| A61B 5/12 | (2006.01) |
| G10L 21/0364 | (2013.01) |

(52) U.S. Cl.
CPC .......... G10L 21/0205 (2013.01); A61B 5/225 (2013.01); A61B 5/6898 (2013.01); G10L 25/69 (2013.01); *A61B 5/123* (2013.01); *G10L 21/0364* (2013.01)

(58) Field of Classification Search
USPC .............. 381/74, 72, 55–59, 61, 77; 700/94; 702/191; 345/156
See application file for complete search history.

(56) References Cited

U.S. PATENT DOCUMENTS

| 7,817,803 B2* | 10/2010 | Goldstein | ............ A61B 5/0002 381/56 |
| 8,155,340 B2* | 4/2012 | Garudadri | ................ H04R 5/04 381/77 |
| 2014/0111415 A1* | 4/2014 | Gargi | ...................... G06F 3/017 345/156 |
| 2015/0086030 A1* | 3/2015 | Moriai | ................ H04M 19/047 381/59 |

FOREIGN PATENT DOCUMENTS

WO    WO 2013180031 A1 * 12/2013 .......... H04M 19/047

* cited by examiner

*Primary Examiner* — MD S Elahee
(74) *Attorney, Agent, or Firm* — Reches Patents

(57) ABSTRACT

Methods and systems are provided for enhancing speech intelligibility in electronic devices. During outputting of acoustic signal via an electronic device, measurement of forces applied by user of the electronic device against the device (or enclosure thereof) may be obtained. The force measurements may be used to assess and/or estimate the listening intelligibility experienced by the user. Further, the force measurements may be used to control or adjust a listening intelligibility stage applied during generation and/or processing of the acoustic signals that are outputted via the electronic device. In some instances, an audio input, corresponding to ambient noise affecting intelligibility, may be obtained, and may be used to control or assist in controlling the listening intelligibility stage.

20 Claims, 7 Drawing Sheets

SPEECH INTELLIGIBILITY DETECTION

CLAIM OF PRIORITY

This patent application makes reference to, claims priority to and claims benefit from the U.S. Provisional Patent Application No. 61/843,396, filed on Jul. 7, 2013, which is hereby incorporated herein by reference in its entirety.

TECHNICAL FIELD

Aspects of the present application relate to audio processing. More specifically, certain implementations of the present disclosure relate to methods and systems for speech intelligibility detection.

BACKGROUND

Existing methods and systems for providing audio processing, particularly for enhancing speech intelligibility, may be inefficient and/or costly. Further limitations and disadvantages of conventional and traditional approaches will become apparent to one of skill in the art, through comparison of such approaches with some aspects of the present method and apparatus set forth in the remainder of this disclosure with reference to the drawings.

BRIEF SUMMARY

A system and/or method is provided for speech intelligibility detection, substantially as shown in and/or described in connection with at least one of the figures, as set forth more completely in the claims.

These and other advantages, aspects and novel features of the present disclosure, as well as details of illustrated implementation(s) thereof, will be more fully understood from the following description and drawings.

DETAILED DESCRIPTION

Certain example implementations may be found in method and system for non-intrusive noise cancellation in electronic devices, particularly in user-supported devices. As utilized herein the terms "circuits" and "circuitry" refer to physical electronic components (i.e. hardware) and any software and/or firmware ("code") which may configure the hardware, be executed by the hardware, and or otherwise be associated with the hardware. As used herein, for example, a particular processor and memory may comprise a first "circuit" when executing a first plurality of lines of code and may comprise a second "circuit" when executing a second plurality of lines of code. As utilized herein, "and/or" means any one or more of the items in the list joined by "and/or". As an example, "x and/or y" means any element of the three-element set $\{(x), (y), (x, y)\}$. As another example, "x, y, and/or z" means any element of the seven-element set $\{(x), (y), (z), (x, y), (x, z), (y, z), (x, y, z)\}$. As utilized herein, the terms "block" and "module" refer to functions than can be performed by one or more circuits. As utilized herein, the term "example" means serving as a non-limiting example, instance, or illustration. As utilized herein, the terms "for example" and "e.g.," introduce a list of one or more non-limiting examples, instances, or illustrations. As utilized herein, circuitry is "operable" to perform a function whenever the circuitry comprises the necessary hardware and code (if any is necessary) to perform the function, regardless of whether performance of the function is disabled, or not enabled, by some user-configurable setting.

Figure 1A:
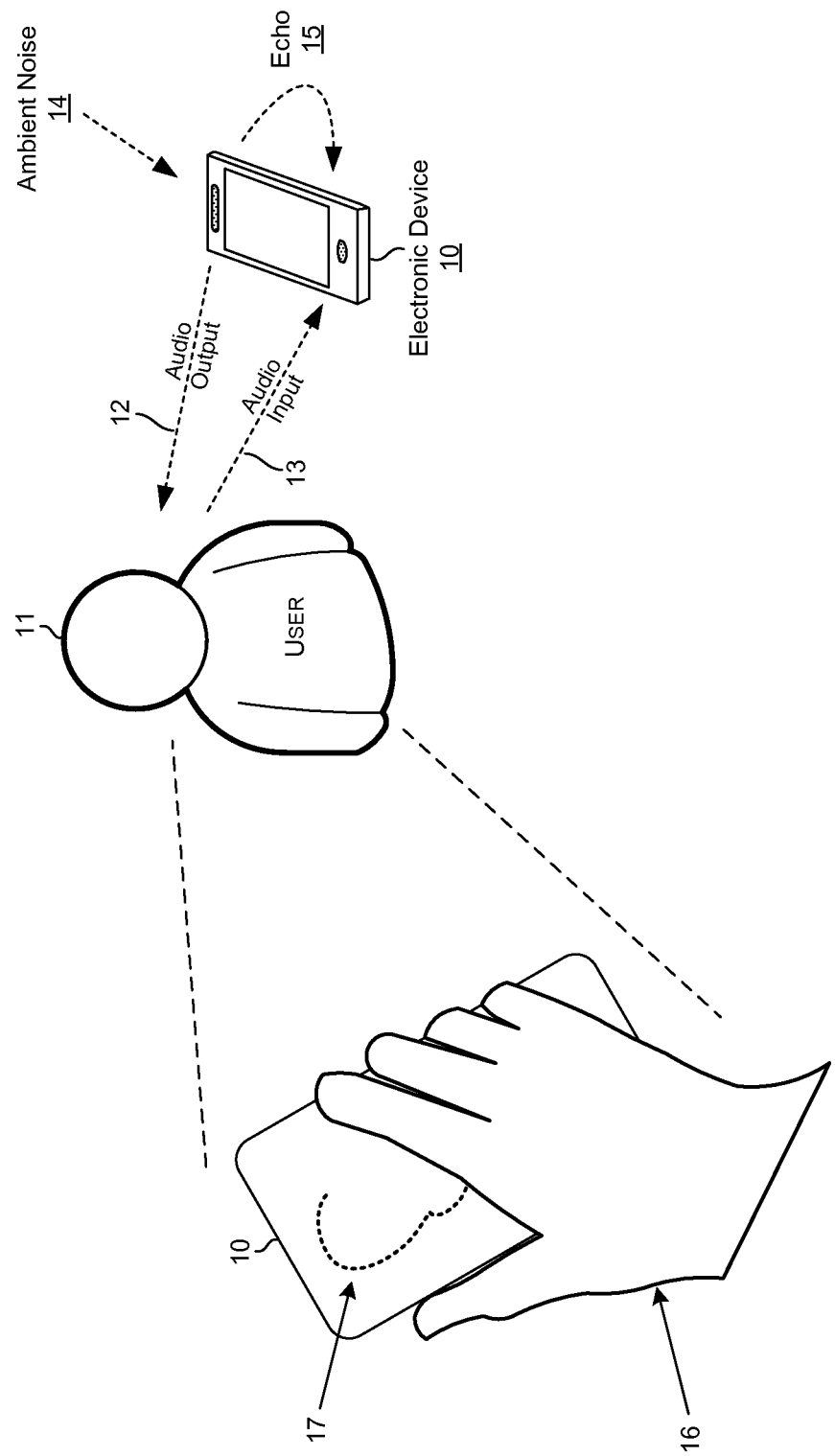
FIG. 1A illustrates an example electronic device, which may be configured to support audio intelligibility detection and enhancement based on force measurements.

FIG. 1A illustrates an example electronic device, which may be configured to support audio intelligibility detection and enhancement based on force measurements. Referring to FIG. 1A, there is shown an electronic device 10.

The electronic device 10 may comprise suitable circuitry for implementing various aspects of the present disclosure. In this regard, the electronic device 10 may be configurable, for example, to perform or support various functions, operations, applications, and/or services. The functions, operations, applications, and/or services performed or supported by the electronic device 10 may be run or controlled based on pre-configured instructions and/or user interactions with the device.

In some instances, electronic devices, such as the electronic device 10, may support communication of data, such as via wired and/or wireless connections, in accordance with one or more supported wireless and/or wired protocols or standards.

In some instances, electronic devices, such as the electronic device 10, may be a mobile and/or handheld device—i.e., intended to be held or otherwise supported by a user (e.g., user 11) during use of the device, thus allowing for use of the device on the move and/or at different locations. In this regard, an electronic device may be designed and/or configured to allow for ease of movement, such as to allow it to be readily moved while being held by the user as the user moves, and the electronic device may be configured to perform at least some of the operations, functions, applications and/or services supported by the device while the user is on the move.

In some instances, electronic devices may support input and/or output of acoustic signals (e.g., sound, ultrasound, infrasound, and vibration). For example, the electronic device 10 may incorporate one or more acoustic output components (e.g., speakers, such as loudspeakers, earpieces, bone conduction speakers, and the like) and one or more acoustic input components (e.g., microphones, bone conduction sensors, and the like), for use in outputting and/or inputting (capturing) audio and/or other acoustic content, and/or suitable circuitry for handling acoustic functions (e.g., driving, controlling and/or utilizing the acoustic input/ output components) and/or for processing signals (and/or data corresponding thereto) outputted or captured by these components.

Examples of electronic devices may comprise communication devices (e.g., corded or cordless phones, mobile phones including smartphones, VoIP phones, satellite phones, etc.), handheld personal devices (e.g., tablets or the like), computers (e.g., desktops, laptops, and servers), dedicated media devices (e.g., televisions, audio or media players, cameras, conferencing systems equipment, etc.), and the like. In some instances, electronic devices may be wearable devices—i.e., they may be worn by the device's user rather than being held in the user's hands. Examples of wearable electronic devices may comprise digital watches and watch-like devices (e.g., iWatch), glasses-like devices (e.g., Google Glass), or any suitable wearable listening and/or communication devices (e.g., Bluetooth earpieces). The disclosure, however, is not limited to any particular type of electronic device.

In operation, the electronic device 10 may be used to perform various operations, including acoustic related operations—e.g., in outputting and/or outputting acoustic signals, such as sound and/or vibration signals. For example, the electronic device 10 may be used in outputting acoustic signals (e.g., audio, which may comprise speech and/or other audio). In this regard, the electronic device 10 may obtain data comprising audio content (e.g., from remote sources, such as during voice calls and/or downloads, and/or from local sources, such as internal or external media storage devices), may process the data to extract the audio content therein, and may convert the audio content to signals suited for outputting (e.g., audio output 12, provided to the user 11), such as via suitable output components (e.g., a loudspeaker, an earpiece, a bone conduction speaker, and the like).

Similarly, the electronic device 10 may be used for inputting acoustic signals (e.g., audio, which may comprise speech and/or other audio). In this regard, the electronic device 10 may capture acoustic signals (e.g., audio input 13, which may be provided by the user 11), such as via suitable input components (e.g., a microphone, a bone conduction sensor, and the like). The captured signals may then be processed, to generate corresponding (audio) content, which may be consumed within the electronic device 10 and/or may be communicated (e.g., to other device(s), local or remote).

The quality of audio (or acoustic signals in general) outputted by and/or inputted into (captured by) electronic devices may be affected by and/or may depend on various factors. For example, audio quality may depend on the resources being used (transducer circuitry, transmitter circuitry, receiver circuitry, network, etc.) and/or environmental conditions. The audio quality may also be affected by noise—e.g., where electronic devices are used in noisy environments. A noisy environment may be caused by various conditions, such as wind, ambient audio (e.g., other users talking in the vicinity, music, traffic, etc.), and the like. All these conditions combined may be described hereinafter as ambient noise (an example of which is shown in FIG. 1A, as the reference 14). Another factor that may affect audio quality, particularly during input operations, is echo. In this regard, acoustic echo (an example of which is shown in FIG. 1A as echo 15) may occur in a system when an acoustic (e.g., audio) signal, such as speech, is outputted by the system (e.g., via an acoustic output component thereof, such as a loudspeaker), and that signal (or portion thereof) is picked up by an acoustic input component (e.g., microphones) of the system. For example, the echo 15 may comprise a delayed, filtered and/or distorted version of the signal(s) outputted by the electronic device 10 (e.g., the audio output 12). Thus, in the example scenario depicted in FIG. 1A, audio data (e.g., content) generated by the electronic device 10, based on signals captured by the electronic device 10 (e.g., corresponding to the audio input 13), may include unwanted component corresponding to the picked up echo 15.

In some instances, listening experiences of users of electronic devices (e.g., user 11 of the electronic device 10) may vary, such as based on conditions affecting quality, and variations therein. Users may react to their listening experiences (and variations therein) by adjusting the manner by which they may interact (physically) with their electronic devices. For example, in an example audio use scenario in which user 11 may use the electronic device 10 to receive audio (e.g., during a voice call), the user 11 may hold the electronic device 10, using the user's hand 16, and may press the electronic device 10 to the user's head, particularly pressing the part of the electronic device 11 where audio is outputted (e.g., where the earpiece is located) against the user's ear 17. The intelligibility of the audio that the user 11 experiences may be influenced by various factors relating to the audio and/or any transfer thereof—e.g., spoken clarity, explicitness, lucidity, comprehensibility, perspicuity, noise embedded in the audio, distortion, partial loss, etc. The intelligibility of the audio may also be affected by local conditions, such as ambient noise 14 and/or echo 15. The user 11 may react to the intelligibility of the audio by pressing the electronic device 10 against the user's ear 17. In this regard, the user 11 may exert a variable amount of force, by adjusting the pressure applied by the user's hand 16 onto the electronic device when pressing it against the user's ear 17 for example, in order to optimize the speech intelligibility experienced by the user 11. Increasing the pressure in this manner may enhance speech intelligibility by minimizing the acoustic leakage between the speaker signal and the ear-canal when conditions so require. If the intelligibility and quality of the speech is low then the user 11 may apply more force such that the leakage between the loudspeaker and ear-canal is reduced and as a result, intelligibility is increased.

Accordingly, in various implementations of the present disclosure, audio operations may be configured to incorporate speech intelligibility enhancement, which may be based on, at least in part, measurement or estimation of forces applied by users against at least a part of the devices or systems used in outputting to acoustic signals. In this regard, the application of forces may be considered as being pre-operational to, and as such may be used as estimation of perceived listening quality experienced by the users. Further, the measurements of these forces (and metrics derived therefrom) may be used to control the manner by which acoustic outputs may be adjusted to enhance the users' listening intelligibility.

Figure 1B:
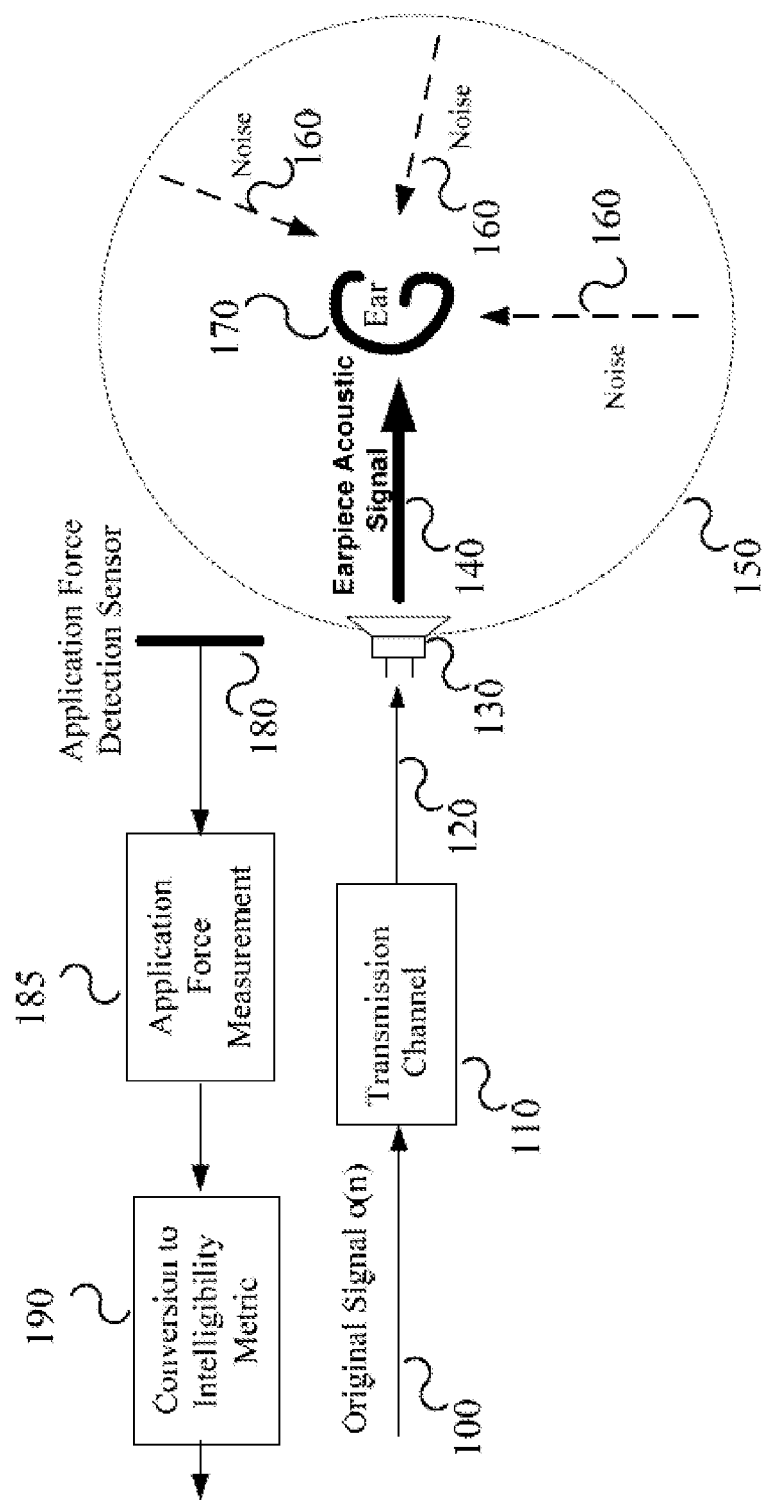
FIG. 1B is a block diagram illustrating example intelligibility measurement using an application force sensor.

FIG. 1B is a block diagram illustrating example intelligibility measurement using an application force sensor. Referring to FIG. 1B, there is shown example use of an application force sensor to generate force measurement resulting for interactions of user, such as in response to reception of audio (or quality thereof).

As shown in FIG. 1B, an original audio signal 100 may be sent through a transmission channel 110. A resulting/corresponding signal 120 may be then effectively applied to an end device loudspeaker 130, with a corresponding loudspeaker output 140 being, for example, an acoustic signal that is applied to a user's ear 170. In some instances, speech imperfections may be present in the loudspeaker output 140, with these speech imperfections occurring or being caused at any or all of the steps 100, 110, 120, and 130—e.g., during generation of the original audio signal 100, communication through the transmission channel 110, handling of the signal 120, and/or outputting via the loudspeaker 130. For example, the original signal 100 may be distorted due to the speaker being too loud or too soft or noisy due to ambient conditions surrounding the talker (e.g., at the far-end). The transmission channel 110 may introduce noise and/or jitter, as well as cause lost signals and/or fading signal effects. The signal at the near-end 120 may be further distorted by the receiving circuits of the device and the loudspeaker 130 may further distort the signal. In addition, ambient conditions 150 at the user's ear 170 may introduce noise and interference from a variety of sources 160.

In an example implementation, an application force detector 180 may be used to detect forces applied by the user (e.g., pressure that the user is applying on the device), and output of the application force detector 180 may be processed—e.g., be applied to an application force measurement block 185. For example, the application force measurement block 185 may derive a measurement signal based upon the output of the application force detector 180, and the measurement signal derived by the application force measurement block 185 may be further processed—e.g., by inputting to a conversion to intelligibility metric block 190, where the measurement signal may be converted into a metric signal. The metric signal may relate to the force applied by a user (e.g., a user's hand, as described with respect to FIG. 1A and/or the user's ear as described with respect to both FIGS. 1A and 1B). The metric signal may be related to (and as such may be used as indication of) the intelligibility of the acoustic signal as experienced by the user. It is important to note that each listener may apply a different application force (even under the same conditions) and/or that different force may be applied (even by the same listener) in different conditions. Hence, the application force to metric conversion and interpretation may be optimized and calibrated for different users and/or different conditions by monitoring each user's behavior continuously and/or in different conditions. The present implementation may be used, for example, in any listening device used in earpiece mode, where a loudspeaker is applied to the ear of the listener, and where the listener will instinctively vary the application force on the device to optimize the leakage between the ear canal and loudspeaker. In addition, the metric itself may be used not only by the user's host device but also could be used by other devices and systems by transmitting the metric using appropriate transmission channels.

Figure 2:
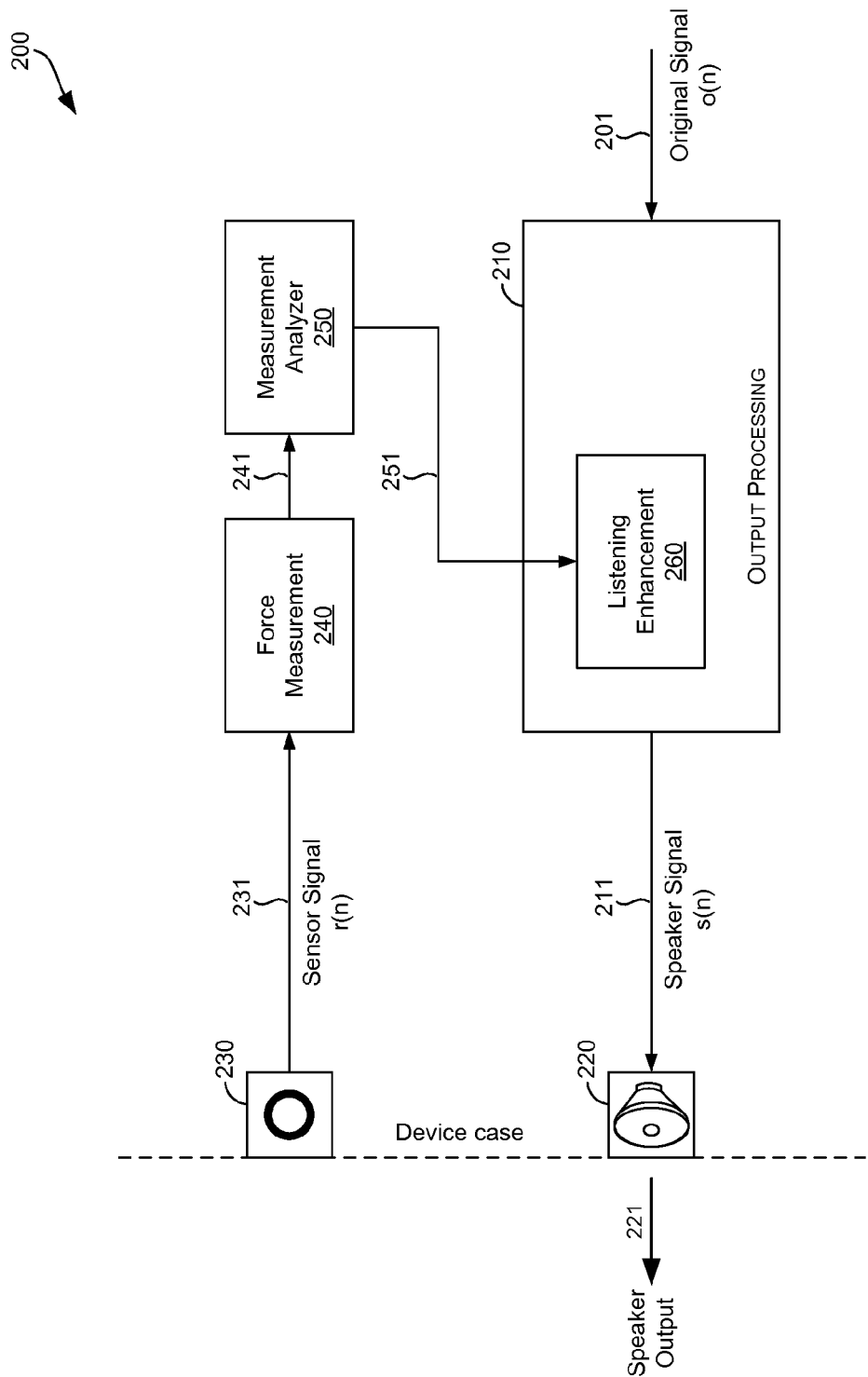
FIG. 2 illustrates an example system that may support audio intelligibility detection and enhancement based on force measurements using a force sensor.

FIG. 2 illustrates an example system that may support audio intelligibility detection and enhancement based on force measurements using a force sensor. Shown in FIG. 2 is system 200.

The system 200 may comprise suitable circuitry for use in outputting and/or inputting audio, and/or for providing adaptive assessment and/or enhancement thereof, particularly audio intelligibility detection, assessment, and enhancement, based on force measurements. For example, system 200 may be incorporated into and/or be implemented in an electronic device (e.g., the electronic device 10 of FIG. 1A) to provide adaptive audio intelligibility detection and enhancement therein. Thus the system 200 may correspond to the electronic device 10 (or portions thereof) when that device is utilized during outputting of acoustic signals (e.g., speech or other audio), with that output being adaptively controlled based on application of force by the user onto the device (e.g., pressing user's ear onto the device, to enhance the listening experience of the user). The force measurements used to support audio (e.g., speech) intelligibility detection, assessment, and enhancement in the system 200 may be obtained using force sensors (e.g., integrated into and/or attached to an enclosure or a case of a device incorporating the system 200).

For example, as shown in the example implementation depicted in FIG. 2, the system 200 may comprise an output processing block 210, a speaker 220, a force sensor 230, a force measurement block 240, a measurement analyzer 250, and a listening enhancement block 260.

The output processing block 210 may comprise suitable circuitry for generating acoustic signals, which may be configured for outputting via particular acoustic output devices or components (e.g., the speaker 220). In this regard, the output processing block 210 may be configured, for example, to apply various signal processing functions to convert an original (digital) input (e.g., signal 201) into analog acoustic based signals that are particularly suitable for output operations in the speaker 220. Thus, in the example implementation depicted in FIG. 2, the output processing block 210 may be operable to generate a speaker signal s(n) 211, which may be configured for output via the speaker 220.

The listening enhancement block 260 may comprise suitable circuitry for assessing and/or optimizing output acoustic signals generated via the output processing block 210, such as to enhance listening intelligibility by listeners. In particular, the listening enhancement block 260 may be configured to assess or estimate quality of output audio (e.g., listening intelligibility). The assessment or estimation of quality of audio may be based on, for example, metrics that may be perceived as being indicative of quality of audio as subjectively experienced by the user. For example, metrics relating to forces applied by the user onto the case of the device (e.g., pressure applied by user's ear) may be used as indication of perceived quality of audio. Further, the listening enhancement block 260 may be configured to utilize various methods for improving the quality (e.g., speech intelligibility) of acoustic signals outputted by system 200. For example, the listening enhancement block 260 may be configured to enhance the listening intelligibility (e.g., based on assessment of quality of output audio) by increasing effective signal to noise ratio of the speech signals. The disclosure is not limited to any particular form of listening intelligibility enhancement, however, and any suitable enhancement technique may be used and/or applied (e.g., via the listening enhancement block 260).

The force sensor 230 may be configurable to detect application of forces, generating a corresponding sensor signal r(n) 231. For example, the force sensor 230 may be operable to detect pressure that a user may be applying on the system 200 (or a device comprising that system), such as by pressing the user's ear against a case of the system (or the device comprising the system).

The force measurement block 240 may comprise suitable circuitry for determining or obtaining force measurement(s), corresponding to be force(s) applied to the system 200 (or any enclosure comprising the system), such as by a user of the system. For example, the force measurement block 240 may be operable to process the sensor signal r(n) 231 outputted by the force sensor 230, to derive correspondingly a measurement signal 241 based upon the detected force(s).

The measurement analyzer 250 may comprise suitable circuitry for processing force measurements, as obtained via the force measurement block 240 for example, such as to convert these measurement into metrics that may be utilized in conjunction with audio output operations. For example, the metrics may be used in assessing various characteristics (e.g., quality related characteristics, such as listening intelligibility) of the audio output(s), and/or in adaptively controlling and/or adjusting acoustic related functions (e.g., processing done during acoustic output related operations). The measurement analyzer 250 may be configured to analyze, for example, force measurements corresponding to application of force by users of the system 200 (as detected via the force sensor 230), to enable obtaining or generating force measurement related metrics.

In operation, the system 200 may be utilized to output acoustics, such as audio (e.g., speech), and to provide during such output operations enhanced listening intelligibility, based on force measurements. The audio output may correspond to an original input signal o(n) 201, which may correspond to "far-end" audio (e.g., audio originating from a remote source, a far-end peer, which may be communicating the audio through a transmission channel to a device incorporating the system 200), or may be a near-end audio or speech—e.g., audio generated in the same device that incorporates the system 200. The original signal o(n) 201 may be processed via the output processing block 210, to generate the speaker signal s(n) 211, which may be configured specifically to be suitable for output via the speaker 220. The output 221 from the speaker 220 may comprise acoustic signals that would be applied to ears of user of the system 200.

In some instances, quality of audio (e.g., listening intelligibility), as experienced by the user, may be degraded (e.g., resulting in speech imperfections), due to various conditions and/or factors affecting the different stages of audio generation, transmission, processing and/or outputting. For example, original audio (audio used to generate the original input signal o(n) 201) may be distorted due to the far-end speaker being too loud or too soft, or too noisy due to ambient conditions surrounding the talker at the far-end side. The transmission channels used in communicating the audio may introduce noise and jitter, as well as lost or fading signal effects. The speaker signal s(n) 211 generated via the output processing block 210 may be distorted, such as in circuitry used in receiving the audio, and the speaker 220 may further distort the signal. Further, ambient conditions at the listener's ear at the near-end side may introduce noise and interference from a variety of ambient sources.

Accordingly, quality of audio (e.g., listening intelligibility) may be assessed, and/or enhanced, such as by applying adjustments to the audio output to counteract and/or mitigate effects of at least some of the conditions affecting listening intelligibility. For example, the listening enhancement block 260 may be used to assess listening intelligibility, and/or to determine and/or apply such listening intelligibility within the output processing block 210, when generating the speaker signal s(n) 211. In particular, the listening intelligibility enhancement may be configured, for example, based on force measurements corresponding to particular actions of the user (listeners) that may be interpreted as being indicative of the quality of the listening intelligibility as experienced by the user. For example, in situations where the user may experience degradation in listening intelligibility, the user may react by pressing against the user's ear, the case or enclosure of a device containing the system 200 (e.g., near the area where the speaker 220 is located, in attempt to block ambient noise). Thus, the bigger the force the user applies against the case or enclosure, generally the less listening intelligibility would likely be experienced by the user.

In the example implementation depicted in FIG. 2, the force sensor 230 may be used to detect the pressure that the user is applying on the device (or its case). The force sensor 230 may generate, in response, the sensor signal r(n) 231, which may be applied to the force measurement block 240. The force measurement block 240 may process the sensor signal r(n) 231, to derive measurements corresponding to the applied force (e.g., estimating the force applied by the user, and/or changes thereto in the course of active listening) The corresponding measurement signal 241 may then be inputted to measurement analyzer 250, where it is converted into audio related metrics. The audio related metrics may be provided as control input 251 to the listening enhancement block 260, for use thereby in assessing listening intelligibility and/or in controlling the listening enhancement (e.g., being used to determine and/or apply suitable adjustments, by the listening enhancement block 260, to the audio output in order to enhance listening intelligibility experienced by the user). Thus, the listening intelligibility may be assessed, and/or may be adjusted (for enhancement thereof) based on the force applied by the user (e.g., by pressing the user's ear), which in turn is related to the intelligibility of the acoustic signals as experienced by the user.

It is important to note that each listener may apply a different application force in different conditions. Hence, the application force to metric conversion and interpretation could be optimized and calibrated for different users by monitoring the user's behavior continuously in different conditions. This can be implemented in any listening device used in earpiece mode, where the loudspeaker is applied to the ear of the listener, and where the listener will instinctively vary the application force on the device to optimize the leakage between the ear canal and loudspeaker. In addition, the metric itself can be used not only by the user's host device but also could be used by other devices and systems by transmitting the metric using appropriate transmission channels.

Figure 3:
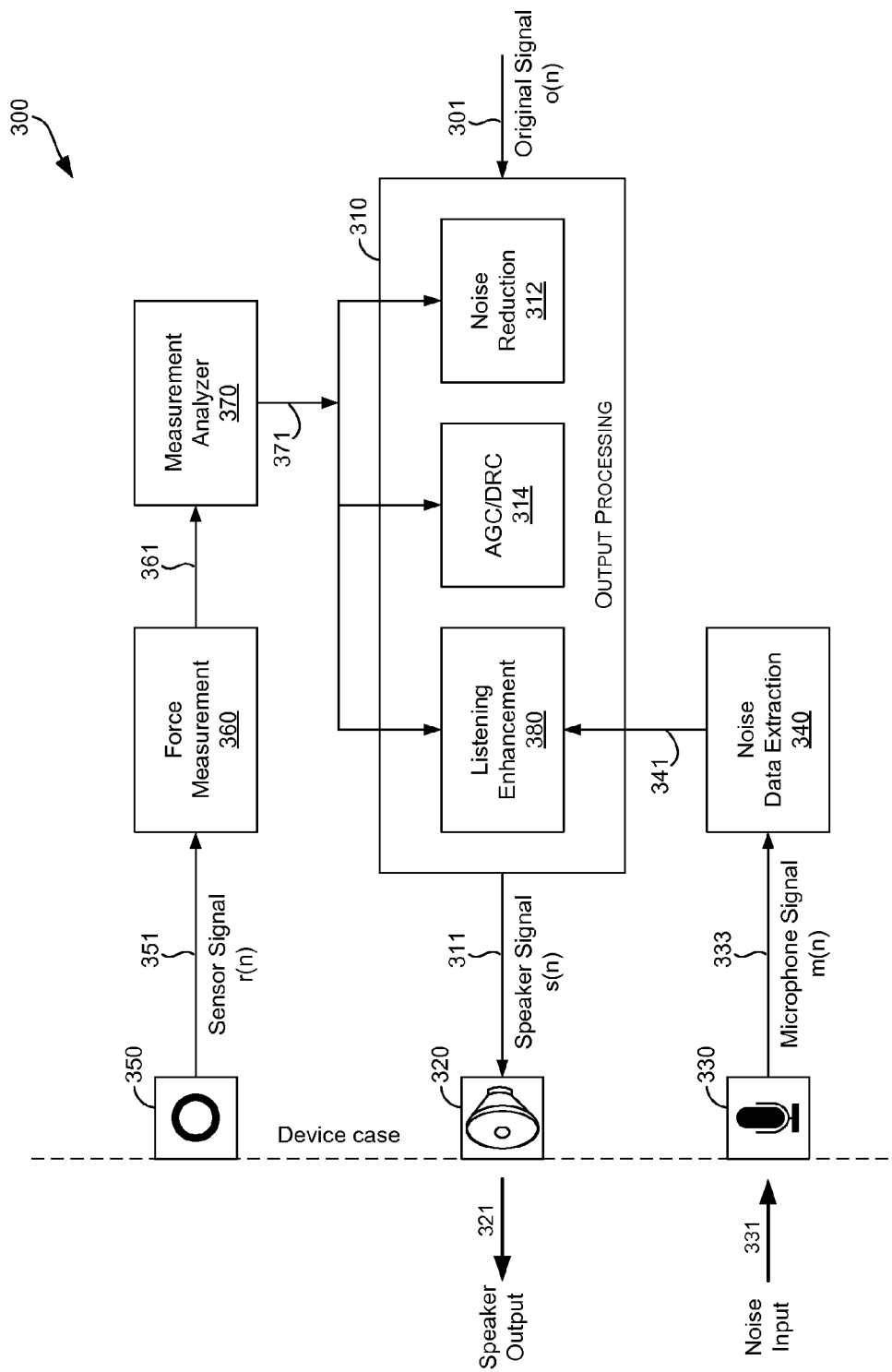
FIG. 3 illustrates an example system that may support audio intelligibility detection and enhancement based on force measurements using a force sensor and based on audio feedback.

FIG. 3 illustrates an example system that may support audio intelligibility detection and enhancement based on force measurements using a force sensor and based on audio feedback. Shown in FIG. 3 is system 300.

The system 300 may be substantially similar to the system 200 of FIG. 2. In this regard, the system 300 may comprise suitable circuitry for use in outputting and/or inputting audio, and/or for providing adaptive enhancement associated therewith, particularly audio intelligibility detection and enhancement based on force measurements. Thus, as with the system 200 of FIG. 2, the system 300 may also be incorporated into and/or be implemented in an electronic device (e.g., the electronic device 10 of FIG. 1A) to provide adaptive audio intelligibility detection and enhancement therein, whereby acoustic (audio) output may be assessed and/or adaptively controlled based on force (or measurement thereof) that may be applied by the user onto the device. In addition to use of force detection and/or measurement to assess and/or estimate quality of audio (particular listening intelligibility), and/or determine and apply corresponding processing adjustments, however, the system 300 may further be configured to also monitor ambient noise (e.g., using acoustic input elements) and to use data relating to monitored ambient noise to further enhance the listening intelligibility.

For example, as shown in the example implementation depicted in FIG. 3, the system 300 may comprise an output processing block 310, a speaker 320, a microphone 330, a noise data extraction block 340, a force sensor 350, a force measurement block 360, and a measurement analyzer 370.

Each of the speaker 320, a microphone 330, the force sensor 350, the force measurement block 360, and the measurement analyzer 370 may, for example, be similar to the corresponding component in the system 200 of FIG. 2—that is the speaker 220, the force sensor 230, the force measurement block 240, and the measurement analyzer 250.

The noise data extraction block 340 may comprise suitable circuitry for processing signals (e.g., acoustic signals, captured via the microphone 330 for example), to provide noise related analysis of the signals (e.g., presence and characteristics of noise), and/or to generate noise related data (e.g., metrics), such as to provide data that may be used for adaptive noise based control of audio output operations in the system 300. The noise data extraction block 340 may be configured to analyze, for example, microphone signals m(n) 333, corresponding to captured input 331 which may comprise, at least in part, ambient noise, to enable obtaining or generating ambient noise related parameters.

The output processing block 310 may be operable to process acoustic outputs, as described with respect to the output processing block 210 of the system 200 of FIG. 2 for example. In this regard, the output processing block 310 may comprise suitable circuitry for generating acoustic signals, which may be configured for outputting via particular acoustic output devices or components (e.g., the speaker 320). The output processing block 310 may be configured, for example, to apply various signal processing functions to convert an original (digital) input (e.g., signal 301) into analog acoustic based signals that are particularly suitable for output operations in the speaker 320. In the example implementation depicted in FIG. 3, the output processing block 310 may be operable to generate a speaker signal s(n) 311, which may be configured for output via the speaker 320.

The output processing block 310 may be configured to assess, and/or apply various measures for optimizing and/or enhancing, quality of acoustic outputs of the system 300. For example, the output processing block 310 may comprise a noise reduction block 312, an automatic gain control (AGC) and dynamic range compression (DRC) block 314 and a listening enhancement block 380. In this regard, the noise reduction block 312 may be operable to determine and/or apply noise reduction measures (e.g., based on estimation of ambient noise), and the AGC/DRC block 314 may be operable to apply automatic gain control and/or and dynamic range compression to generated acoustic outputs, such as based on quality related parameters as determined by the system 300 or provided thereto (e.g., by the user).

The listening enhancement block 380 may be substantially similar to the listening enhancement block 260 of FIG. 2, for example. In this regard, the listening enhancement block 380 may comprise suitable circuitry for assessing or estimating quality of output audio of the system 300, and/or for optimizing output acoustic signals generated via the output processing block 310, such as to enhance listening intelligibility by listeners. The listening enhancement block 380 may assess or estimate quality of output audio (e.g., listening intelligibility), such as based on metrics which may be indicative of quality of audio experienced by the user (e.g., metrics relating to forces applied by the user, onto the case of a device comprising the system 300). Further, listening enhancement block 380 may support use of various methods for enhancing intelligibility of acoustic (e.g., speech) signals outputted by system 300. For example, in particular, as with the listening enhancement block 260 of FIG. 2, the listening enhancement block 380 may be configured to enhance the listening intelligibility based on assessment of quality of audio using force measurements and/or metrics determined based thereon. However, the listening enhancement block 380 may be operable to additionally utilize noise related data to further enhance listening enhancement block 380, such as by determining adjustments based on ambient noise as well as based on metrics determined using measurement of force applied by the users (or changes thereto).

In operation, the system 300 may be utilized to output acoustics (e.g., audio, such as speech), and to provide assessment and/or enhancement of listening intelligibility during such output operations, (e.g., based on force measurements), substantially as described with respect to the system 200 of FIG. 2 for example. Further, the system 300 may be configured to utilize ambient noise to further improve and/or optimize listening intelligibility enhancement provided thereby.

In an example use scenario, ambient noise 331 may be detected by the microphone 330. The resulting microphone output m(n) 333 may be applied to the input of the noise data extraction block 340, which may extract or determine ambient noise parameters, and may send that data to the listening enhancement block 380. The listening enhancement block 380 may then attempt to apply noise based listening intelligibility related adjustments to signals it receives from the AGC/DRC block 314, such that the speaker signal 311 applied to the speaker 320 would incorporate such adjustments. Thus, the output signal 321 from the speaker 320 may comprise acoustic signals providing enhanced intelligibility to the user in the presence of the ambient noise 331.

The adjustments determined and/or applied by the listening enhancement block 380 may also be based on force measurements. In this regard, the force applied to the system 300 (or any device incorporating it) may be detected by the force sensor 350. The application of force may correspond to, for example, the user pressing his/her ear against the area where the speaker 320 is located (or vice versa), to provide enhancing listening experience. The sensor output r(n) 351 of the force sensor 350 is inputted to the force measurement block 360, which may convert the sensor output into measurement data relating to the detected force. The measurement data may, in turn, be inputted to measurement analyzer 370, which may convert the measurement data into intelligibility related metrics, which may be provided as metrics output signal 371. The metrics output signal 371, comprising intelligibility related metrics, may then be used in assessing quality of audio (particularly listening intelligibility) and/or for determining adjustments that may be applied to the various acoustics outputting stages, such as noise reduction (via the noise reduction block 312), gain and/or compression (via the AGC/DRC block 314), and listening intelligibility enhancement (via the listening enhancement block 380). Thus, using force detection based metrics may enable improving speech intelligibility.

The listening intelligibility assessment and/or enhancement, as provided by the system 300, may be performed in dynamic and/or adaptive manner. In this regard, the continued detection of force (and ambient noise) may provide dynamic and/or direct feedback—e.g., changes in pressure detected may be treated as enhancement feedback, indicating the success of intelligibility enhancement applied by the system 300, as pressure applied by the user may tend to lessen as the intelligibility improve.

The listening intelligibility assessment and/or enhancement, as provided by the system 300, may also be performed and/or configured based on quality of the original signals (based on which the acoustic outputs are generated), and to further rely on feedback indications to optimize handling of the original signals. For example, in the case of a noisy received original signal 301, noise reduction block 312 may be configured to apply noise reduction in a feedback based manner—e.g., configured to optimize the listening quality with force (pressure) based metrics being used as real time feedback of the quality of the noise reduction. Similarly, in the case of the received audio signal being low or distorted, the parameters of the AGC/DRC block 314 may be configured to provide dynamic adjustments, using force (pressure) based metrics as real time feedback of the quality of the gain and/or compression performed by the AGC/DRC block 314.

Figure 4:
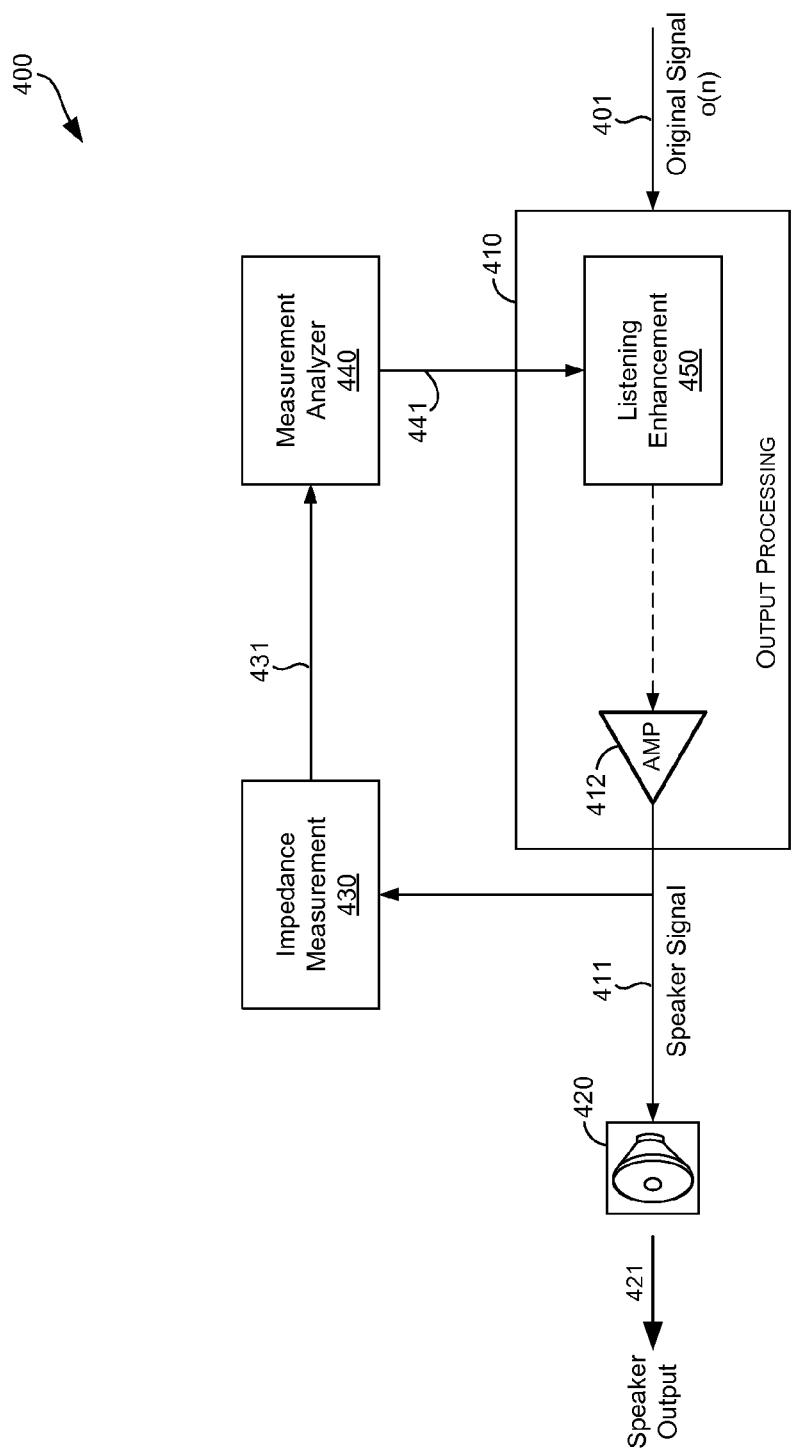
FIG. 4 illustrates an example system that may support audio intelligibility detection and enhancement based on force measurements using impedance variations of an audio speaker.

FIG. 4 illustrates an example system that may support audio intelligibility detection and enhancement based on force measurements using impedance variations of an audio speaker. Shown in FIG. 4 is system 400.

The system 400 may be substantially similar to the system 200 of FIG. 2. In this regard, the system 400 may comprise suitable circuitry for use in outputting and/or inputting audio, and/or for providing adaptive enhancement associated therewith, particularly audio intelligibility detection and enhancement. Thus, as with the system 200 of FIG. 2, the system 400 may also be incorporated into and/or be implemented in an electronic device (e.g., the electronic device 10 of FIG. 1A) to provide adaptive audio intelligibility detection and enhancement therein, whereby acoustic (audio) output may be adaptively controlled based on force (or measurement thereof) that may be applied by the user onto the device. However, rather than using direct force detection (e.g., using dedicated force sensors), as it is the case with systems 200 and 300 of FIGS. 2 and 3, the system 400 may be configured to obtain measurements indicative of force applied by users indirectly. In particular, the system 400 may be configured to determine (or estimate) force measurements based on tracking of certain characteristics and/or parameters of signals driving acoustic output components.

In some example implementations, as an alternative to directly measuring the force applied by the user (e.g., pressure applied to or by the user's ear, when the user presses a device comprising the system 400), variations in the impedance of acoustic output components (e.g., speaker, bone conduction transducer, etc.) may be measured and/or tracked. Thus, the impedance (and variations therein) of acoustic output components may be used as an indication of applied forces (and variations therein).

For example, the system 400 may correspond to an example implementation of a speaker-based system providing listening enhancement based on force measurements obtained from measuring and tracking of impedance of a speaker. The system 400 may comprise, e.g., an output processing block 410, a speaker 420, an impedance measurement block 430, a measurement analyzer 440, and a listening enhancement block 450.

The output processing block 410 may comprise suitable circuitry for generating acoustic signals, which may be configured for outputting via the speaker 420. The output processing block 410 may be configured, for example, to apply various signal processing functions to convert an original (digital) input (e.g., signal 401) into analog acoustic based signals that are particularly suitable for output operations in the speaker 420. The processing performed via the output processing block 410 may comprise application of amplification, via a drive amplifier 412. The output processing block 410 may be operable to generate a speaker signal 411, which may be configured for output via the speaker 420.

The impedance measurement block 430 may comprise suitable circuitry for determining or obtaining force measurement related data, corresponding to be force(s) applied to the system 400 (or any enclosure comprising the system), such as by a user of the system. In this regard, the impedance measurement block may be operable to determine (or estimate) applied forces based variations in the impedance of the speaker 420. Thus, the impedance measurement block 430 may receive the speaker signal 411 used to drive the speaker 420, and may process that signal to determine impedance of the speaker 420.

The measurement analyzer 440 may comprise suitable circuitry for processing force measurements, as obtained via the impedance measurement block 430 for example, such as to convert these measurements into metrics that may be used in adaptively controlling and/or adjusting acoustic related functions (e.g., processing done during acoustic output related operations). In this regard, the measurement analyzer 440 may be configured to analyze, for example, force measurements corresponding to application of force by users of the system 400 (e.g., as estimated via the impedance measurement block 430, based on variations in the impedance of the speaker 420), to enable obtaining or generating force measurement related metrics.

The listening enhancement block 450 may be substantially similar to the listening enhancement block 260 of FIG. 2. In this regard, the listening enhancement block 450 may comprise suitable circuitry for assessing or estimating quality of output audio of the system 400, and/or for optimizing output acoustic signals generated via the output processing block 410, such as to enhance listening intelligibility by listeners. The listening enhancement block 450 may assess or estimate quality of output audio (e.g., listening intelligibility), such as based on metrics which may be indicative of quality of audio experienced by the user. As shown in the example implementation depicted in FIG. 4, the listening enhancement block 450 may be implemented within the output processing block 410, so that the output processing may incorporate a listening enhancement stage, whereby, listening intelligibility may be enhanced and/or optimized. The listening enhancement block 450 may be support use of various methods for enhancing intelligibility of acoustic (e.g., speech) signals outputted by system 400. For example, In particular, as with the listening enhancement block 260 of FIG. 2, the listening enhancement block 450 may be configured to enhance the listening intelligibility based on force measurements and/or metrics determined based thereon. However, the force measurements used to provide the metrics driving the quality assessment and/or the adaptive adjustments (e.g., based on such assessment) determined and/or applied by the listening enhancement block 450 may be based on tracking of impedance (e.g., of speaker 420) rather than direct force detection. Nonetheless, the difference in the mechanisms by which metrics are obtained may not impact the functions or implementation of the listening intelligibility enhancement, and as such the listening enhancement block 450 may operate in substantially the same manner as the listening enhancement block 260 of FIG. 2.

In operation, the system 400 may be utilized to output acoustics (e.g., audio, such as speech), and to provide enhanced listening intelligibility during such output operations, (e.g., based on force measurements), substantially as described with respect to the system 200 of FIG. 2. Nonetheless, the force measurements may be obtained in the system 400 indirectly (e.g., without direct force detection), such as based on impedance of the speaker 420 (or variations therein).

In an example use scenario, the listening enhancement block 450 may be used in applying listening intelligibility related adjustments to output signals, such that the speaker signal 411 applied to the speaker 420 would incorporate such adjustments. Thus, the output signal 421 from the speaker 420 may comprise audio signals providing enhanced intelligibility to the user in the presence of the ambient noise 431. The adjustments determined and/or applied by the listening enhancement block 450 may be based on impedance-based force measurements. For example, the output processing performed in the system 400 may comprise application of amplification via the drive amplifier 412, to amplify the speaker signal 411 presented to the speaker 420. As the user applies more pressure to the enclosure of the speaker 420, the impedance of the speaker 420 may change. Such variation in the speaker impedance may be tracked and/or measured by the impedance measurement block 430. The measurement analyzer 440 may then analyze the impedance-based measurements, converting them to speech related metrics, which may be provided to the listening enhancement block 450. The listening enhancement block 450 may use the metrics to determine (and apply) listening intelligibility related adjustments (thus enhancing the listening experience of the user).

Figure 5:
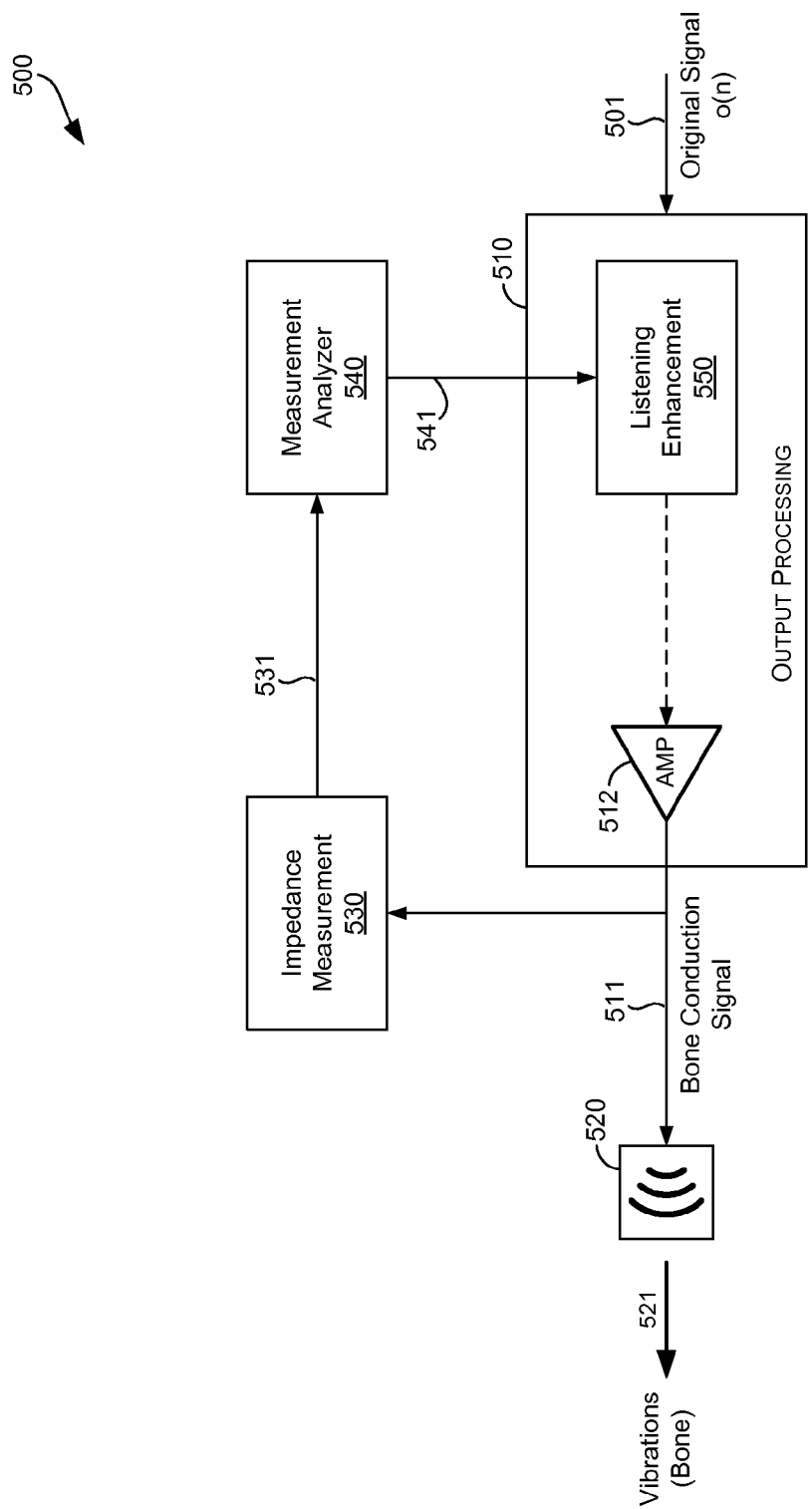
FIG. 5 illustrates an example system that may support audio intelligibility detection and enhancement based on force measurements using impedance variations of a bone conduction transducer.

FIG. 5 illustrates an example system that may support audio intelligibility detection and enhancement based on force measurements using impedance variations of a bone conduction transducer. Shown in FIG. 5 is system 500.

The system 500 may be substantially similar to the system 400 of FIG. 4, for example. In this regard, the system 500 may comprise suitable circuitry for use in outputting and/or inputting audio, and/or for providing adaptive enhancement associated therewith, including audio intelligibility detection and enhancement, based on force measurements that are determined or estimated indirectly, such as from measuring or tracking of certain characteristics and/or parameters of signals driving acoustic output components. In particular, as with the system 400 of FIG. 4, the system 500 may also be configured to indirectly measure forces applied by the user (e.g., pressure applied to or by the user's body, when the user presses a device comprising the system 500) based on measuring and/or tracking of impedance (and variations therein) of acoustic output components. However, the system 500 may correspond to an example implementation of a bone conduction based system providing listening enhancement based on force measurements obtained from measuring and tracking of impedance of a bone conduction transducer. In this regard, the system 500 may comprise an output processing block 510, a bone-conduction transducer 520, an impedance measurement block 530, a measurement analyzer 540, and a listening enhancement block 550.

The output processing block 510 may be similar to the output processing block 410 of FIG. 4 for example. The output processing block 510 may be configured, however, for supporting acoustic outputs via bone-conduction elements. In this regard, the output processing block 510 may comprise suitable circuitry for generating acoustic signals, which may be configured for outputting via the bone-conduction transducer 520. The processing performed via the output processing block 510 may comprise application of amplification, via a drive amplifier 512. The output processing block 510 may be operable to generate a bone-conduction signal 511, which may be configured for output via the bone-conduction transducer 520.

The impedance measurement block 530 may be similar to the impedance measurement block 430 of FIG. 4 for example. The impedance measurement block 530 may be configured, however, for deriving force measurement based on impedance (and/or variations therein) of bone-conduction elements. In this regard, the impedance measurement block 530 may comprise suitable circuitry for determining or estimating force(s) applied to the system 500 (or any enclosure comprising the system), such as by a user of the system, and/or to generate measurement data corresponding thereto, based on variations in the impedance of the bone-conduction transducer 520. Thus, the impedance measurement block 530 may receive the bone-conduction signal 511 used to drive the bone-conduction transducer 520, and may process that signal to determine impedance of the bone-conduction transducer 520.

The measurement analyzer 540 may be similar to the measurement analyzer 440 of FIG. 4. The measurement analyzer 540 may be configured, however, for analyzing measurements obtained based on tracking of impedance (and/or variations therein) of bone-conduction elements. In this regard, the measurement analyzer 540 may comprise suitable circuitry for processing force measurements, as obtained via the impedance measurement block 530 for example, such as to convert these measurements into metrics that may be used in adaptively controlling and/or adjusting acoustic related functions (e.g., processing done during acoustic output related operations). The measurement analyzer 540 may be configured to analyze, for example, force measurements corresponding to application of force by users of the system 500 (e.g., as estimated via the impedance measurement block 530, based on variations in the impedance of the bone-conduction transducer 520), to enable obtaining or generating force measurement related metrics.

The listening enhancement block 550 may be substantially similar to the listening enhancement block 450 of FIG. 4. In this regard, the listening enhancement block 550 may comprise suitable circuitry for assessing or estimating quality of output audio of the system 400, and/or for optimizing output acoustic signals generated via the output processing block 510, such as to enhance listening intelligibility by listeners, substantially as described with respect to the listening enhancement block 450.

In operation, the system 500 may be utilized to output acoustics (e.g., audio, such as speech), and to provide enhanced listening intelligibility during such output operations, (e.g., based on force measurements), substantially as described with respect to the system 400 of FIG. 4. Nonetheless, the force measurements may be obtained in the system 500 indirectly (e.g., without direct force detection), such as based on impedance of the bone-conduction transducer 520 (or variations therein).

In an example use scenario, the listening enhancement block 550 may be used in applying listening intelligibility related adjustments to output signals, such that the speaker signal 511 applied to the bone-conduction transducer 520 would incorporate such adjustments. Thus, the output signal 521 from the bone-conduction transducer 520 may comprise audio signals providing enhanced intelligibility to the user in the presence of the ambient noise 531. The adjustments determined and/or applied by the listening enhancement block 550 may be based on impedance-based force measurements. For example, the output processing performed in the system 500 may comprise application of amplification via the drive amplifier 512, to amplify the bone-conduction signal 511 presented to the bone-conduction transducer 520. As the user applies more pressure to the enclosure of the bone-conduction transducer 520, the impedance of the bone-conduction transducer 520 may change. Such variation in the speaker impedance may be tracked and/or measured by the impedance measurement block 530. The measurement analyzer 540 may then analyze the impedance-based measurements, converting them to speech related metrics, which may be provided to the listening enhancement block 550. The listening enhancement block 550 may use the metrics to determine (and apply) listening intelligibility related adjustments (thus enhancing the listening experience of the user).

In some implementations, metrics derived from application of force measurement and/or impedance measurement may be utilized for other/additional uses (beside listening enhancement). For example, a metric derived in accordance with the present disclosure may be used as a quality indicator, and may be communicated with other devices—e.g., transferred to the far-end peers, so that the sending device could carry out available remedial actions, such as changing the voice coding, reducing or increasing the microphone gain, or changing parameters of the noise cancellation, for example. Also, if the device in which the measurements are obtained is part of a network (e.g., cellular network, WLAN, etc.), metrics may be reported to a network controller, for use therein as an indicator of reception quality, thus allowing the network controller to take, where possible, available remedial actions (e.g., forcing a handoff, improving the voice coding scheme, or other network enhancements). Further, in such network-based user scenarios, force detection based metrics may also be used as quality of service (QoS) indicators, thus aiding in the collection of quality statistics.

Figure 6:
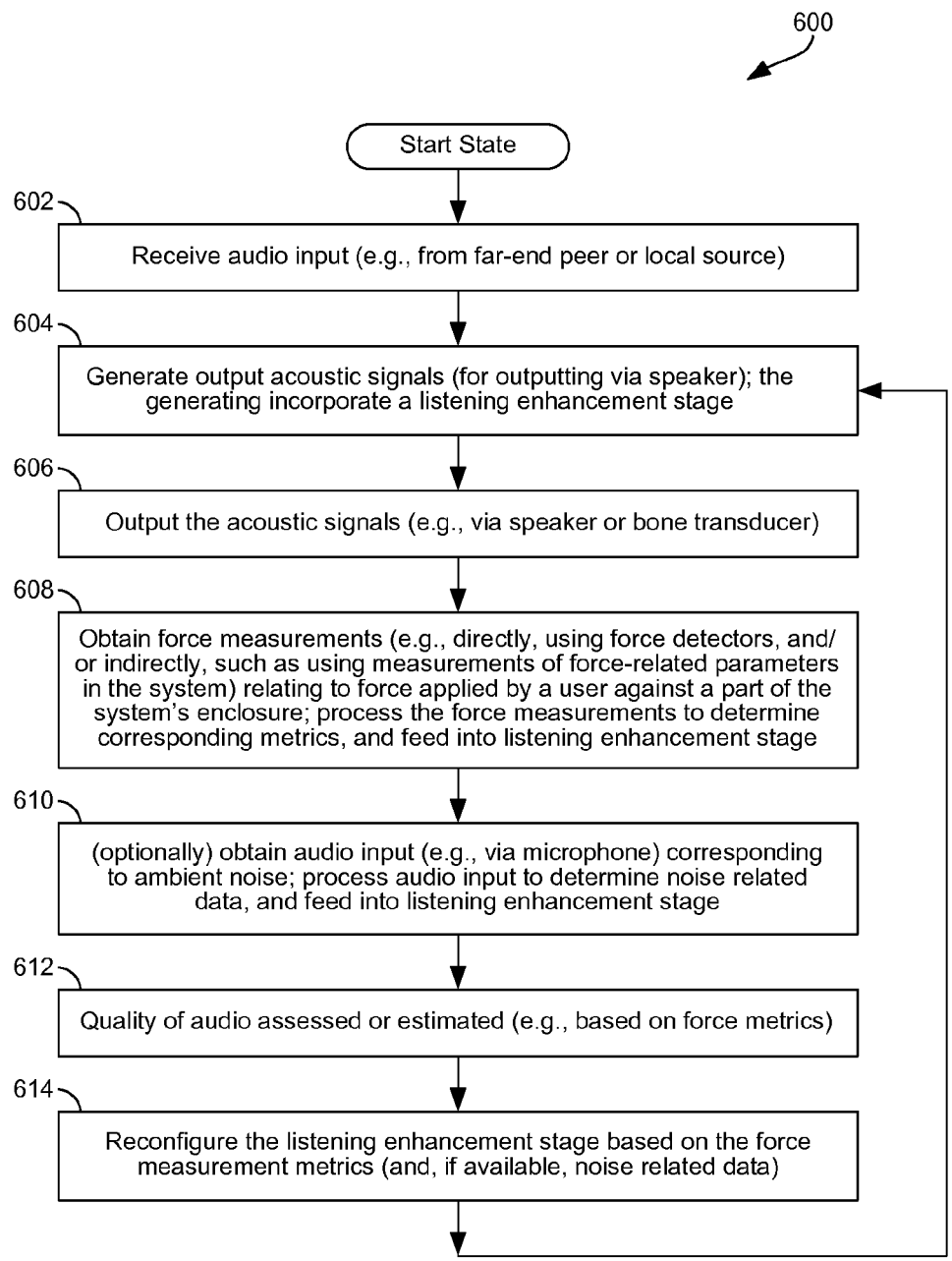
FIG. 6 is a flowchart illustrating an example process for providing audio intelligibility detection and enhancement based on force measurements.

FIG. 6 is a flowchart illustrating an example process for providing audio intelligibility detection and enhancement based on force measurements. Shown in FIG. 6 is flow chart 600, comprising a plurality of example steps, which may be executed in a system (e.g., one of the systems 200, 300, 400, and 500 of FIGS. 2 to 5) to provide audio (e.g., speech) intelligibility detection and enhancement.

After a starting step, in which the system may be powered on and/or setup for audio related operations (e.g., for reception of signals carrying audio content, extracting content, processing and/or outputting of audio, etc.), audio input may be received (e.g., from a far-end source and/or from a local source) in step 602.

In step 604, output acoustic signals (for outputting via speaker or a bone-conduction transducer) corresponding to the audio input may be generated. In this regard, generating the output acoustic signals may incorporate a listening enhancement stage, configured to enhance listening intelligibility as experienced by the user.

In step 606, the acoustic signals may be outputted (e.g., via the speaker, or the bone-conduction transducer).

In step 608, force measurements may be obtained (e.g., directly, such as via dedicated force detection, using the force sensors 230 or 350 and force measurement blocks 240 and 360 for example; or indirectly, such as based on measurement of parameters that may be affected by applied forces—e.g., speaker or bone-conduction transducer impedance, using impedance measurement block 430 or 530), corresponding to force(s) applied by user of the system against a part of the system's enclosure. In this regard, the application of force(s) (and variations therein) may be treated as indicative of perceived quality of audio (particularly listening intelligibility) by the user. The force measurements may be processed (e.g., using the measurement analyzers 250, 370, 440, or 540), such as to determine corresponding metrics, which may be fed into the listening enhancement stage applied during generation of output acoustic signals.

In step 610, audio input may be obtained (e.g., via a microphone, such as the microphone 330), corresponding to ambient noise affecting listening intelligibility experienced by the user. The audio input may then be processed (e.g., via the noise data extraction block 340), to determine noise related data, with the corresponding data being fed into the listening enhancement stage applied during generation of output acoustic signals.

In step 612, quality of output audio (e.g., listening intelligibility) may be assessed and/or estimated. The assessment or estimation of quality of audio may be based on, for example, metrics that may be perceived as being indicative of quality of audio as subjectively experienced by the user. For example, quality of audio may be assessed or estimated based on force related metrics derived from the forces measurements which were obtained directly and/or indirectly (in step 608).

In step 614, the listening enhancement stage may then be reconfigured and/or adjusted based on the force measurement related metrics and (when available) noise related data, and the process may loop back to continue processing of input audio and generation (and outputting) of output acoustic signals based thereon.

Nonetheless, while steps 608-614 are shown as 'following' the outputting of acoustic signals done in step 606, these steps may actually be done in parallel and/or independently of each other—i.e., obtaining the force measurements (and, when done, audio input corresponding to ambient noise) may be continually done, as long as audio handling is ongoing, with corresponding data feeds (and reconfiguration of listening enhancement stage based thereon) being done dynamically and continually.

Other implementations may provide a non-transitory computer readable medium and/or storage medium, and/or a non-transitory machine readable medium and/or storage medium, having stored thereon, a machine code and/or a computer program having at least one code section executable by a machine and/or a computer, thereby causing the machine and/or computer to perform the steps as described herein for non-intrusive noise cancellation.

Accordingly, the present method and/or system may be realized in hardware, software, or a combination of hardware and software. The present method and/or system may be realized in a centralized fashion in at least one computer system, or in a distributed fashion where different elements are spread across several interconnected computer systems. Any kind of computer system or other system adapted for carrying out the methods described herein is suited. A typical combination of hardware and software may be a general-purpose computer system with a computer program that, when being loaded and executed, controls the computer system such that it carries out the methods described herein. Another typical implementation may comprise an application specific integrated circuit or chip.

The present method and/or system may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form. Accordingly, some implementations may comprise a non-transitory machine-readable (e.g., computer readable) medium (e.g., FLASH drive, optical disk, magnetic storage disk, or the like) having stored thereon one or more lines of code executable by a machine, thereby causing the machine to perform processes as described herein.

While the present method and/or system has been described with reference to certain implementations, it will be understood by those skilled in the art that various changes may be made and equivalents may be substituted without departing from the scope of the present method and/or system. In addition, many modifications may be made to adapt a particular situation or material to the teachings of the present disclosure without departing from its scope. Therefore, it is intended that the present method and/or system not be limited to the particular implementations disclosed, but that the present method and/or system will include all implementations falling within the scope of the appended claims.

I claim:

1. A method, comprising:
   in an electronic device:
   outputting acoustic signals;
   obtaining a measurement input corresponding to a force applied by a hand of a user of the electronic device, onto the electronic device or a portion thereof, wherein applying the force by the hand of the user is in response, at least in part, to reception of the acoustic signals by the user; and
   processing the measurement input, to generate acoustic metrics corresponding to an assessment of quality of the reception of the acoustic signals.

2. The method of claim 1, wherein the measurement input comprises an estimate of the pressure applied by the hand of the user against the electronic device or the portion thereof.

3. The method of claim 1, comprising obtaining the measurement input via a force sensor in the electronic device; wherein the force sensor differs from an acoustic input element.

4. The method of claim 1, comprising obtaining the measurement input based on tracking of impedance of an acoustic output element used in outputting the acoustic signals.

5. The method of claim 4, comprising estimating the force applied by a user of the electronic device, to the electronic device or a portion thereof, based on the impedance of the acoustic output element and/or adjustments thereto.

6. The method of claim 1, comprising:
   obtaining an acoustic input corresponding to ambient noise in proximity of the user of the electronic device; and
   processing the acoustic input to determine ambient noise data.

7. The method of claim 6, comprising adaptively controlling the outputting of the acoustic signals based on the determined ambient noise data.

8. The method of claim 1, comprising adaptively controlling the outputting of the acoustic signals based on the generated acoustic metrics.

9. The method of claim 8, wherein the adaptive control of outputting of the acoustic signals comprises adjustments to enhance listening intelligibility.

10. The method of claim 8, wherein the adaptive controlling comprises applying dynamic time-scale modifications to the acoustic signals.

11. The method of claim 1, wherein the acoustic metrics comprise parameters related to one or more of indication of speech intelligibility, distortion, noise, and/or partial loss.

12. The method of claim 1, comprising communicating the acoustic metrics to at least one electronic device.

13. The method of claim 12, wherein the communicated acoustic metrics causes the least one electronic device to adjust one or more functions and/or parameters in the least one electronic device, based on the acoustic metrics.

14. The method of claim 13, wherein the one or more functions and/or parameters are acoustic signal generation related functions and/or parameters.

15. The method of claim 12, wherein the least one electronic device is configured as control element in a network comprising the electronic device, and the acoustic metrics are used by the least one electronic device as indication of quality.

16. The method of claim 15, wherein the least one electronic device is configured to take, in response to assessing acoustic metrics as indication of quality, actions in the network for enhancing quality.

17. The method of claim 15, wherein the least one electronic device is configured to update, in response to assessing acoustic metrics as indication of quality, quality data relating to the network.

18. A system, comprising:
   one or more circuits for use in an electronic device, the one or more circuits being operable to:
   output acoustic signals;
   obtain a measurement input corresponding to a force applied by a hand of a user of the electronic device, onto the electronic device or a portion thereof, wherein applying the force by the hand of the user is in response, at least in part, to reception of the acoustic signals by the user; and
   process the measurement input, to generate acoustic metrics corresponding to an assessment of quality of the reception of the acoustic signals.

19. The system of claim 18, wherein the measurement input comprises an estimate of pressure applied by the hand of the user against the electronic device or the portion thereof.

20. The system of claim 18, wherein the measurement input is obtained based on detection, by a force sensor of the applied force and/or tracking of impedance of an acoustic output element used in outputting the acoustic signals; wherein the force sensor differs from an acoustic input element.

* * * * *